(12) United States Patent
Saunders et al.

(10) Patent No.: US 7,056,020 B2
(45) Date of Patent: Jun. 6, 2006

(54) ALIGNMENT SYSTEMS AND METHODS FOR RADIOGRAPHIC IMAGING SYSTEMS

(75) Inventors: Rowland Frederick Saunders, Hartland, WI (US); Kadri Nizar Jabri, Waukesha, WI (US)

(73) Assignee: GE Medical Systemes Global Technology Company, LLC, Waukesha, WI (US)

( * ) Notice: Subject to any disclaimer, the term of this patent is extended or adjusted under 35 U.S.C. 154(b) by 69 days.

(21) Appl. No.: 10/755,074

(22) Filed: Jan. 9, 2004

(65) Prior Publication Data

US 2005/0152502 A1     Jul. 14, 2005

(51) Int. Cl.
*G01D 18/00* (2006.01)

(52) U.S. Cl. ......................................... 378/207; 378/18
(58) Field of Classification Search ................ 378/207, 378/18
See application file for complete search history.

(56) References Cited

U.S. PATENT DOCUMENTS

| | | | |
|---|---|---|---|
| 5,799,059 A | | 8/1998 | Stembridge et al. |
| 6,409,383 B1 | * | 6/2002 | Wang et al. ................. 378/207 |
| 6,460,003 B1 | * | 10/2002 | Kump et al. ................... 702/85 |
| 6,632,020 B1 | | 10/2003 | Kaufhold et al. |
| 6,811,314 B1 | * | 11/2004 | Cresens ....................... 378/207 |

* cited by examiner

*Primary Examiner*—Craig E. Church
*Assistant Examiner*—Jurie Yun
(74) *Attorney, Agent, or Firm*—Dougherty/Clements; Christopher L. Bernard; Peter J. Vogel

(57) ABSTRACT

Phantoms and discrete spatial and frequency methods for quantitatively measuring the alignment of radiographic imaging systems are described. One embodiment comprises phantoms for use in mechanically aligning radiographic imaging systems. These phantoms comprise: a radio-opaque material capable of holding a well-defined edge that allows quantitative image resolution measurements to be obtained thereof; wherein once the quantitative image resolution measurements are obtained, the spatial frequency response of the radiographic imaging system at a given focal plane can be calculated therefrom, thereby defining the mechanical alignment, resolution, and resolution uniformity of the radiographic imaging system. Systems and methods for mechanically aligning radiographic imaging systems, and methods for obtaining a quantitative measurement of the mechanical alignment, resolution and resolution uniformity of radiographic imaging systems, are also disclosed.

8 Claims, 7 Drawing Sheets

ALIGNMENT SYSTEMS AND METHODS FOR RADIOGRAPHIC IMAGING SYSTEMS

FIELD OF THE INVENTION

The present invention relates generally to radiographic imaging systems. More specifically, the present invention relates to systems and methods that allow the mechanical alignment of radiographic imaging systems to be precisely calibrated so that optimal image resolution quality can be achieved therefrom.

BACKGROUND OF THE INVENTION

With applications ranging from diagnostic procedures to radiation therapy, the importance of high-performance medical imaging is immeasurable. As such, new advanced medical imaging technologies continue to be developed. Digital medical imaging techniques represent the future of medical imaging. Digital imaging systems produce far more accurate and detailed images of an object than conventional film-based imaging systems, and also allow further enhancements of the image to be made once an object is scanned.

Tomography is a two-dimensional radiographic imaging technique in which a cross-sectional image of a selected plane in an object is obtained, while details in other planes are blurred. Tomosynthesis is an advanced three-dimensional radiographic imaging technique in which several 2-D images of an object are taken at different angles and/or planes, and then these images are reconstructed as a 3-D image of the volume of the object that was imaged. Unlike conventional x-ray imaging techniques, tomosynthesis provides depth information about an area of interest within an object being imaged, such as a tumor or other anatomy within a patient. Tomosynthesis also enables any number of 2-D tomographic image slices to be reconstructed from a single scanning sequence of x-ray exposures, without requiring additional x-ray imaging, thereby making tomosynthesis a desirable characterization tool.

Generally, in digital tomography systems, an x-ray source is positioned on one side of an object being imaged, while an x-ray detector (i.e., an amorphous silicon flat panel x-ray detector) is positioned on an opposite side thereof. Generally, in amorphous silicon flat panel x-ray detectors, an amorphous silicon array is disposed on a glass substrate, and a scintillator is disposed over, and is optically coupled to, the amorphous silicon array. The x-ray source generally sweeps along a line, arc, circle, ellipse, hypocycloid, or any other suitable geometry, emitting a beam of x-rays towards the scintillator. The scintillator absorbs the x-ray photons and converts them to visible light. The amorphous silicon array then detects the visible light and converts it into electrical charge. The electrical charge at each pixel on the amorphous silicon array is read out and digitized by low-noise electronics, and is then sent to an image processor. Thereafter, a 2-D cross-sectional image is displayed on a display, and may also be stored in memory for later retrieval. A series of 2-D cross-sectional images may be reconstructed using 3-D reconstruction algorithms, to incorporate depth information into a final 3-D image, if desired.

Accurate alignment of the x-ray source with respect to the x-ray detector is critical to good image resolution in radiographic imaging systems. Phantoms are often used for calibrating and/or validating the alignment of film-based x-ray systems, where it is difficult to quantify x-ray levels or signal levels accurately. However, one drawback with film-based x-ray systems is that, generally, they only allow a visual assessment of the image sharpness to be made. Digital radiographic imaging systems, such as digital linear tomography systems, and any other radiographic imaging systems that allow the image to be digitized for numerical analysis, lend themselves to allowing accurate quantitative measurements of the alignment and/or image resolution or sharpness to be obtained. However, there are presently no known quantitative analysis systems and methods that use discrete spatial and frequency methods to precisely align such imaging systems so that optimal images can be obtained therefrom.

Therefore, it would be desirable to have systems and methods that utilize discrete spatial and frequency analysis to accurately quantify the mechanical alignment of radiographic imaging systems, thereby allowing for the precise mechanical alignment thereof so that optimal image resolution can be obtained therefrom. Additionally, it would be desirable to have simple-geometric-shaped phantoms that were useful for such purposes.

SUMMARY OF THE INVENTION

Accordingly, the above-identified shortcomings of existing systems and methods for aligning radiographic imaging systems are overcome by embodiments of the present invention, which relates to radiographic alignment and/or calibration systems and methods that utilize phantoms, and discrete spatial and frequency analysis of the images obtained thereof, to obtain a numerical analysis of the alignment of the system. This invention allows for the precise alignment and/or calibration of such imaging systems so that better image resolution can be achieved than currently possible using existing alignment and calibration systems and methods.

Embodiments of this invention comprise simple-geometric-shaped phantoms that provide critical quantitative quality assurance in radiographic imaging applications. These phantoms may be used for mechanically aligning a radiographic imaging system. These phantoms may comprise: a radio-opaque material capable of holding a well-defined edge that allows quantitative image resolution measurements to be obtained thereof; wherein once the quantitative image resolution measurements are obtained, the spatial frequency response of the radiographic imaging system at a given focal plane can be calculated therefrom, thereby defining the mechanical alignment, resolution, and resolution uniformity of the radiographic imaging system.

These phantoms may comprise an x-ray absorptive material and/or a radio-opaque material such as, but not limited to: tungsten, lead, a lead-tin alloy, tin, steel, and/or epoxy impregnated with a high atomic number filler, among other things.

Embodiments of this invention also comprise systems for mechanically aligning radiographic imaging systems. These systems may comprise: a phantom capable of holding a well-defined edge that allows quantitative image resolution measurements to be obtained thereof; and a measurement system for obtaining quantitative image resolution measurements of the phantom; wherein once the quantitative image resolution measurements of the phantom are obtained, the spatial frequency response of the radiographic imaging system at a given focal plane can be calculated therefrom, thereby defining the mechanical alignment, resolution, and resolution uniformity of the radiographic imaging system.

These systems may further comprise: an alignment system for optimally aligning the radiographic imaging system once the mechanical alignment of the radiographic imaging system is defined.

The radiographic imaging systems may comprises: a film-based imaging system, a digital imaging system, a film-based x-ray system, a digital x-ray system, a linear tomography system, a tomosynthesis system, a computed radiography system, a radiographic imaging system that allows the obtained images to be digitized so that numerical analysis can be made thereof, and/or an x-ray planographic imaging system that allows the obtained images to be digitized so that numerical analysis can be made thereof.

Embodiments of this invention also comprise methods for obtaining a quantitative measurement of the mechanical alignment, resolution, and resolution uniformity of a radiographic imaging system. These methods may comprise: providing a phantom capable of holding a well-defined edge that allows quantitative image resolution measurements to be obtained thereof; obtaining a digital image of the phantom; and analyzing the frequency content of a derivative of an edge of the image of the phantom to obtain a spatial frequency response of the radiographic imaging system, wherein the spatial frequency response represents the quantitative measurement of the mechanical alignment, resolution, and resolution uniformity of the radiographic imaging system.

Analyzing the frequency content of the derivative of the edge of the image of the phantom to obtain the spatial frequency response of the radiographic imaging system may further comprise: measuring the maximum possible resolution of the radiographic imaging system at a given focal plane to obtain a profile of the phantom.

These methods may further comprise the step of: taking the derivative of the profile to obtain the line spread of the radiographic imaging system.

These methods may further comprise the step of: analyzing the frequency content of the line spread to obtain the spatial frequency response of the radiographic imaging system.

These methods may further comprise utilizing a plurality of phantoms at different locations on a detector so that the focal uniformity of an area of the detector can be determined.

Embodiments of this invention also comprise methods for mechanically aligning radiographic imaging systems. These methods may comprise the steps of: (a) providing a phantom capable of holding a well-defined edge that allows quantitative image resolution measurements to be obtained thereof; (b) obtaining a digital image of the phantom; (c) obtaining a quantitative measurement of the mechanical alignment, resolution, and resolution uniformity of the radiographic imaging system; and (d) aligning the radiographic imaging system once the quantitative measurement is obtained.

These methods may further comprise: repeating steps (b)–(d) as necessary until the radiographic imaging system meets a predetermined alignment measurement.

Embodiments of this invention also comprise methods for correcting repeatable alignment errors in tomographic imaging systems. These methods may comprise the steps of: obtaining at least one unprocessed digital image of a phantom; isolating repeatable alignment errors from random alignment errors by utilizing a plurality of unprocessed digital images of the phantom; characterizing each unprocessed digital image of the phantom; and applying a corrections map to the enhanced image to produce a final image substantially free of repeatable alignment errors.

Characterizing each unprocessed digital image of the phantom may comprise utilizing known phantom specifications that have been previously determined.

Further features, aspects and advantages of the present invention will be more readily apparent to those skilled in the art during the course of the following description, wherein references are made to the accompanying figures which illustrate some preferred forms of the present invention, and wherein like characters of reference designate like parts throughout the drawings.

DESCRIPTION OF THE DRAWINGS

The systems and methods of the present invention are described herein below with reference to various figures, in which.

DETAILED DESCRIPTION OF THE INVENTION

For the purposes of promoting an understanding of the invention, reference will now be made to some preferred embodiments of the present invention as illustrated in FIGS. 1–7 and specific language used to describe the same. The terminology used herein is for the purpose of description, not limitation. Specific structural and functional details disclosed herein are not to be interpreted as limiting, but merely as a basis for the claims as a representative basis for teaching one skilled in the art to variously employ the present invention. Any modifications or variations in the depicted structures and methods, and such further applications of the principles of the invention as illustrated herein, as would normally occur to one skilled in the art, are considered to be within the spirit and scope of this invention.

This invention relates to radiographic (i.e., x-ray planographic) alignment systems and methods that utilize phantoms, and discrete spatial and frequency analysis of the images obtained thereof, to obtain a numerical analysis of the alignment of the system. This invention allows such systems to be precisely aligned and calibrated so that optimal image resolution and resolution uniformity can be achieved therefrom. The phantoms utilized in embodiments of this invention comprise simple geometric shapes that allow for critical quantitative quality assessment of radiographic imaging systems.

Figure 2:
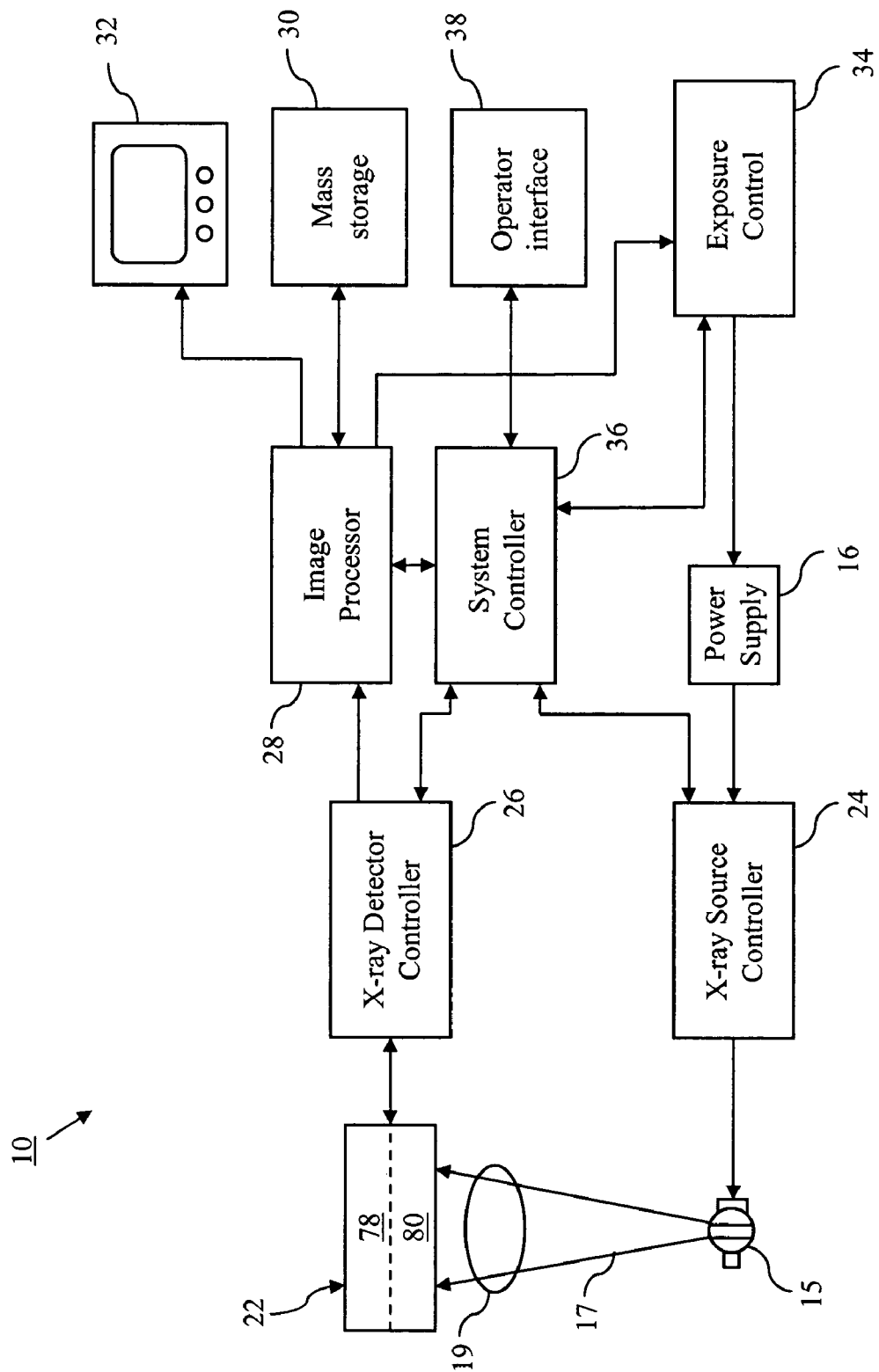
FIG. 2 is a schematic diagram showing the architecture of a digital tomographic imaging system, as utilized in embodiments of this invention.

Referring first to FIG. 2, there is shown a schematic diagram showing the architecture of one exemplary digital tomography system 10, as utilized in some embodiments of this invention. Digital tomography systems 10 generally comprise an x-ray source 15, an x-ray detector 22, an x-ray detector controller 26 that contains electronics for operating the x-ray detector 22, and an x-ray source controller 24 that contains electronics for operating the x-ray source 15. During operation, an overall system controller 36 provides power and timing signals to the x-ray source controller 24, which then controls the operation, sweeping speed, position, projection/shooting angle, etc. of x-ray source 15. X-ray source 15 generally sweeps along a line, arc, circle, ellipse, hypocycloid, or any other suitable geometry, while x-rays 17 are directed from the x-ray source 15 towards the x-ray detector 22, which comprises a scintillator 80 and an amorphous silicon array 78. The overall system controller 36 also controls the operation of the x-ray detector controller 26, which then controls the operation of the x-ray detector 22. After passing through an object being imaged (i.e., a patient 19), the x-rays 17 fall upon scintillator 80, which converts the x-ray photons therein to visible light. The visible light is then converted to an electrical charge by an array of photodiodes 41 in the amorphous silicon array 78. Each photodiode 41 is of large enough area to ensure it will intercept a sizeable portion of the visible light produced by the scintillator 80. Each photodiode 41 also has a relatively large capacitance that allows it to store the electrical charge that results from the photon excitation. A data acquisition system within x-ray detector controller 26 samples analog electrical charge data from the x-ray detector 22, and converts that analog data to digital signals for subsequent processing. The digital signals are then sent to an image processor 28, where the image signal is processed and enhanced. The processed image may then be displayed on a cathode ray tube display 32, or other suitable display, and/or the image can be stored in mass storage 30 for later retrieval. The image processor 28 can also produce a brightness control signal which can be applied to an exposure control circuit 34 to regulate the power supply 16, which can thereby regulate the x-ray source 15 through the x-ray source controller 24. The overall operation of the digital tomography system 10 may be governed by a system controller 36, which may receive commands and/or scanning parameters from an operator via operator interface 38. Operator interface 38 may comprise a keyboard, touchpad, or other suitable input device. An associated cathode ray tube display 32 (or other suitable display) may allow the operator to view the reconstructed image and other data from the image processor 28. The operator supplied commands and parameters may be used by the system controller 36 to provide control signals and information to the image processor 28, the x-ray detector controller 26, the x-ray source controller 24, and/or the exposure control circuit 34.

Embodiments of the present invention may make use of software or firmware running on the system controller 36 to carry out the processing of data in the methods and systems of this invention. A mouse, pointing device, or other suitable input device may be employed to facilitate the entry of data and/or image locations. Other embodiments of this invention may utilize a general purpose computer or workstation having a memory and/or printing capability for storing or printing images. Suitable memory devices are well known and include, but are not limited to, RAM, diskettes, hard drives, optical media, etc. Embodiments using stand-alone computers or workstations may receive data therefrom via conventional electronic storage media and/or via a conventional communications link, and images may then be reconstructed therefrom.

Figure 3:
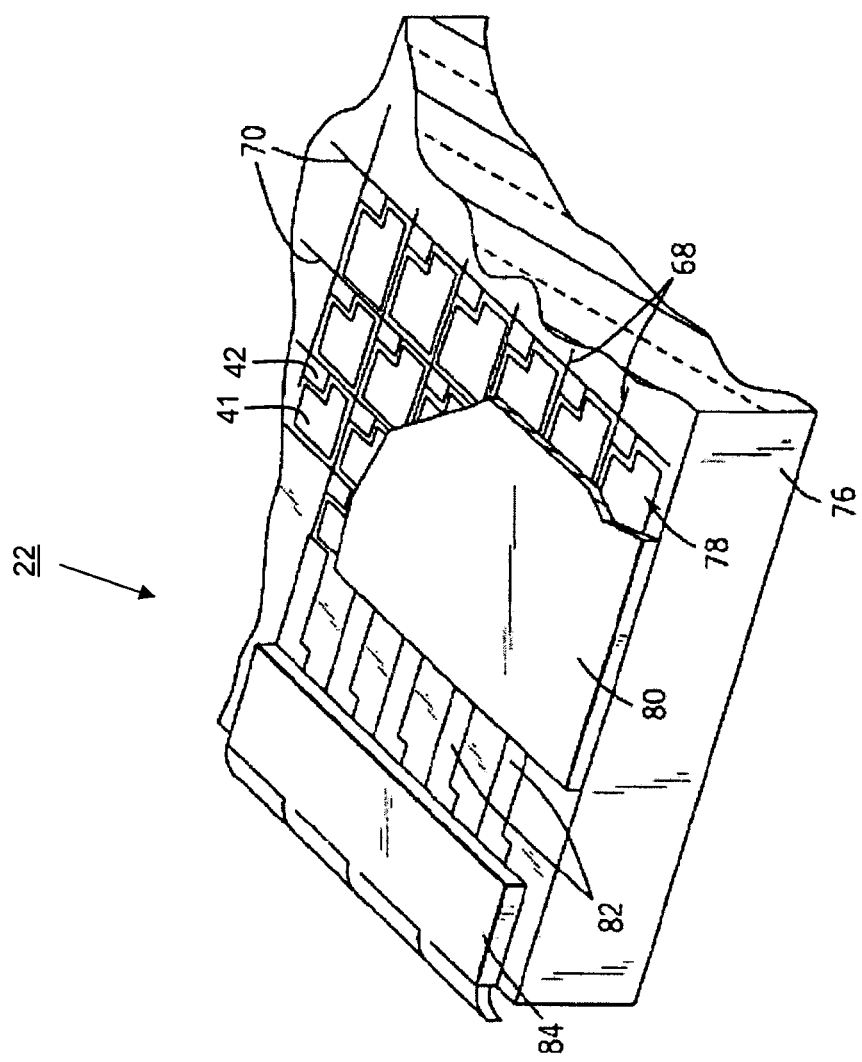
FIG. 3 is a schematic diagram showing the components of a single piece amorphous silicon flat panel, as utilized in embodiments of this invention.

Referring next to FIG. 3, there is shown an exemplary amorphous silicon flat panel x-ray detector 22, as utilized in embodiments of this invention. Generally, column electrodes 68 and row electrodes 70 are disposed on a single piece glass substrate 76, and an amorphous silicon array 78 is defined thereby. The amorphous silicon array 78 comprises an array of photodiodes 41 and field effect transistors (FETs) 42. A scintillator 80 is disposed over the amorphous silicon array 78, and is optically coupled thereto. The scintillator 80, which may comprise a dose-efficient cesium iodide scintillator, receives and absorbs x-ray radiation during operation, and converts the x-ray photons therein to visible light. The high fill factor amorphous silicon array 78, wherein each photodiode 41 therein represents a pixel, converts the detected visible light into an electrical charge. The charge at each pixel is then read out and digitized by low-noise electronics (via contact fingers 82 and contact leads 84), and is thereafter sent to an image processor 28.

Tomographic imaging systems produce an image having a slice thickness that is dependent upon the sweep angle that is used while the image is being acquired. The mechanical alignment and velocity tracking of the x-ray source 15 with respect to the x-ray detector 22 are critical to precise slice thickness and slice depth in the final image. However, it is extremely difficult to directly measure the numerous items that contribute to this alignment. Therefore, one good alternative measurement of the alignment of such systems, as well as many other radiographic imaging systems, can be obtained by indirectly measuring the resulting quality of an image of a known phantom taken therewith.

Phantoms are commonly used in film-based imaging systems to determine the image quality of a resulting image. However, using phantoms with such film-based systems generally only allows for the subjective, qualitative analysis of the resulting image sharpness or quality, and indicate only whether the slice thickness and slice depth are approximately correct. Detailed quantitative analytical results are extremely difficult and beyond the reach of most of these systems and methods.

Currently, there are no acceptable systems and methods for quantitatively evaluating the alignment of radiographic imaging systems and the resolution of the resulting images created thereby. The phantoms and discrete spatial and frequency analysis methods of this invention provide for the quantitative analysis of the alignment of radiographic imaging systems, thereby allowing such imaging systems to be precisely aligned so that optimal image quality can be achieved in the images obtained therefrom.

The resolution of an x-ray detector can be easily measured using a thin radio-opaque bar-shaped phantom that is placed on the surface of the detector. An x-ray image thereof can be acquired, and then a subset of the image can be analyzed by taking the Fast Fourier Transform (FFT) of the derivative of the edge that is formed by the image of the bar. The result of this calculation provides the spatial frequency response of the imaging system, which is one way to define the resolution of the imaging system.

Figure 1:
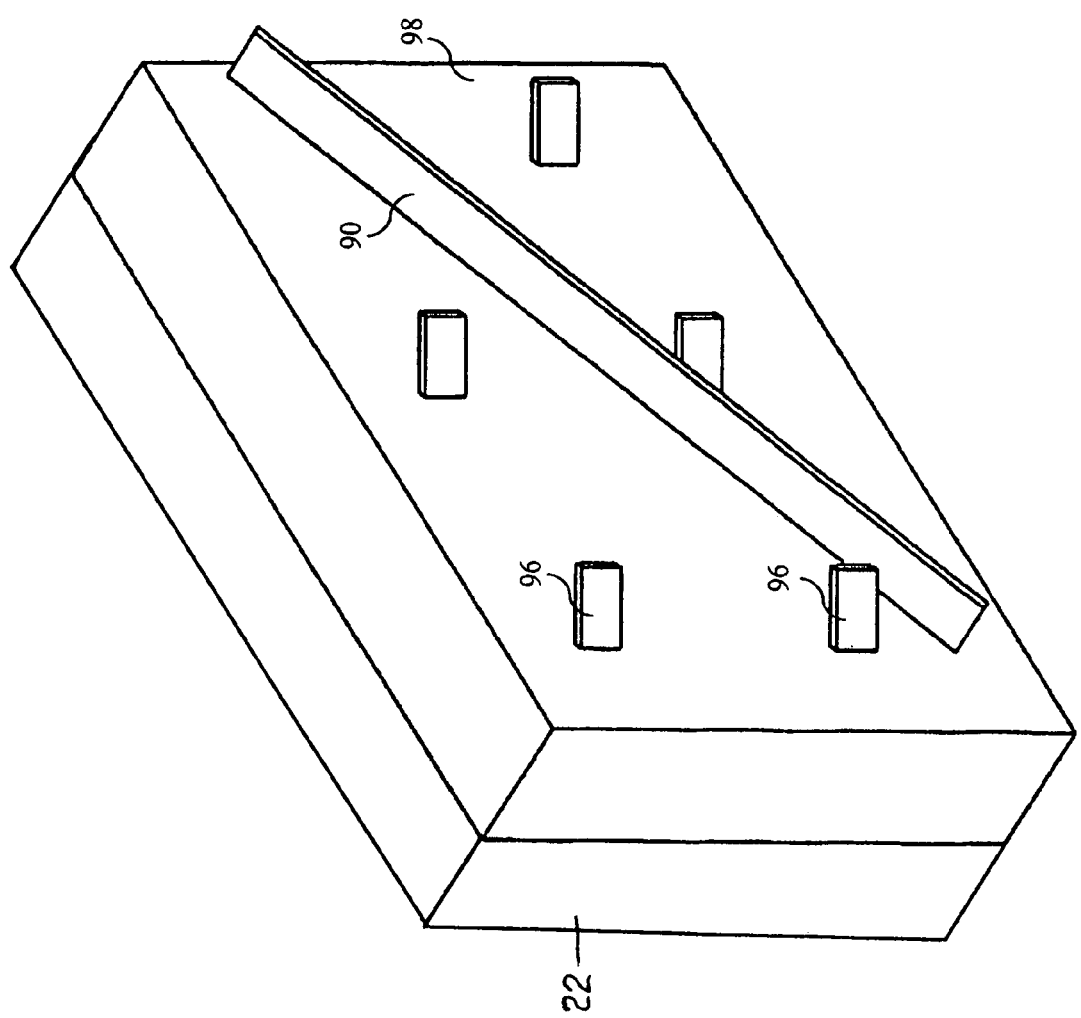
FIG. 1 is a schematic diagram showing some exemplary phantoms, as utilized in embodiments of this invention.

One or more simple-geometric-shaped phantoms may be used to determine the focal depth and focal range of a radiographic imaging system. The phantoms of this invention may comprise any suitable radio-opaque attenuating material that is capable of holding an edge straight enough to allow image resolution measurements to be obtained thereof. Some exemplary non-limiting materials comprise tungsten, lead, lead-tin alloys, tin, steel, and epoxy impregnated with a high atomic number filler. As shown in FIG. 1, embodiments of this invention utilize a radio-translucent support 98 on the detector, wherein the radio-translucent support 98 has a thin bar-shaped phantom 90 positioned thereon at an angle such that the center of the bar is at or near the center of the imaging system. This radio-translucent support 98 may comprise any suitable radio-translucent material, such as for example, low density foam. The long axis of the bar-shaped phantom 90 should be arranged perpendicular to the direction of travel of the x-ray source 15 and/or x-ray detector 22 so that the resulting image provides the best resolution at the focal depth of the imaging system. The quantitative numerical analysis of the resulting image at the point of maximum resolution provides a quantitative measure of the imaging system's performance. The performance at numerous slice depths and sweep angles can be easily measured and compared using this invention.

A static reference image of the phantom 90 can be taken to provide the maximum resolution possible for a particular height in question. The focal spot and inherent detector resolution, as well as the scatter from any attenuating material, can then be determined and later removed from the images. The analysis tools of this invention can be used in any suitable direction (i.e., laterally, longitudinally, etc.).

Figure 4:
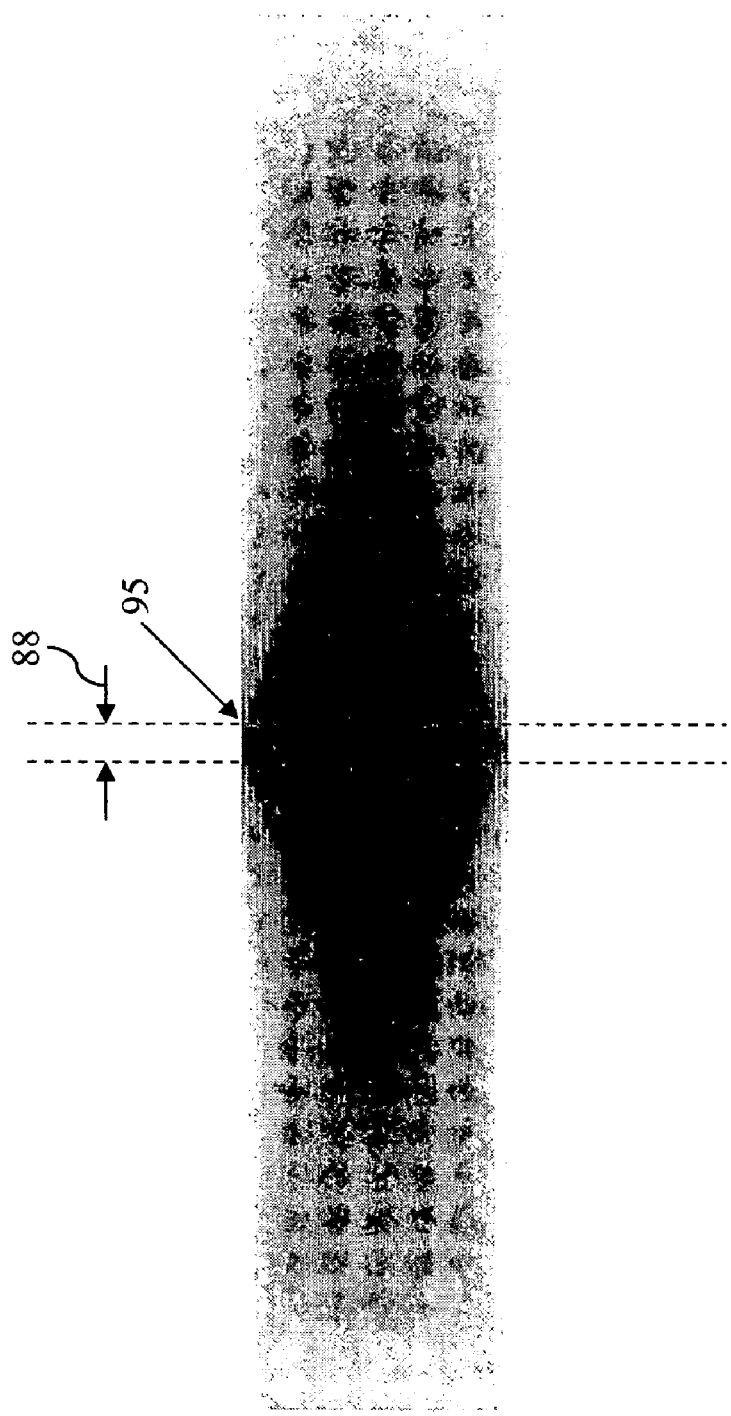
FIG. 4 is a digital tomographic image of the long phantom shown in FIG. 1.

As shown in FIG. 4, the bow-tie shaped image is the resulting tomographic image of the long phantom 90 shown in FIG. 1. The center of this image 88 represents the maximum possible resolution, and corresponds to the focal plane of the imaging system where the edge of the bar is well defined. The edge of the bar begins to blur as the distance from the focal plane increases. The increase in blurring from this maximum possible resolution at the focal plane is determined by the sweep angle used during image acquisition. Ideally, there should be a step change between the signal where the phantom is and the false signal where the phantom isn't, in the vicinity of arrow 95. However, in reality there will not be a step change near arrow 95 because mechanical misalignment issues cause the system resolution to be less than perfect. So, in reality, what you will see is a rectangular profile having softened edges instead of sharp edges.

Figure 5:
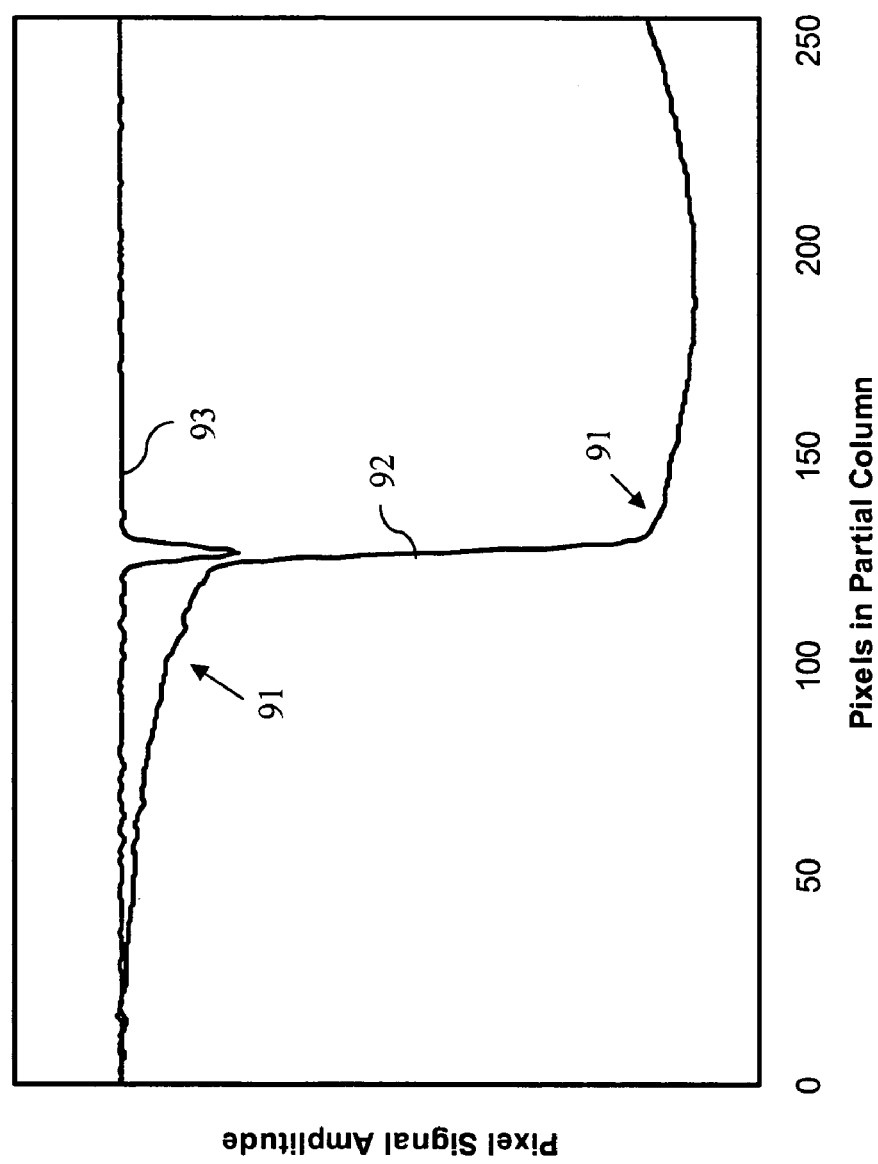
FIG. 5 is a graph showing a cross-sectional profile of the long phantom of FIG. 1 near the focal plane of the digital imaging system, and also showing the line spread function of the imaging system.

Referring now to FIG. 5, there is shown a cross-sectional profile 92 of the long phantom 90 near the focal plane of the digital tomographic imaging system. Ideally, if the phantom is precisely aligned to the centerline of the x-ray source and/or x-ray detector sweep, this profile 92 would have a rectangular shape with sharp edges, not a rounded profile with soft edges as shown at points 91. The focal spot blurs the edges 91 of the phantom 90 to a certain degree, but the mechanical misalignments between the x-ray source 15 and the x-ray detector 22 cause the bulk of the degradation of this image. The derivative of this profile shows the line spread function 93 of this digital imaging system.

Figure 6:
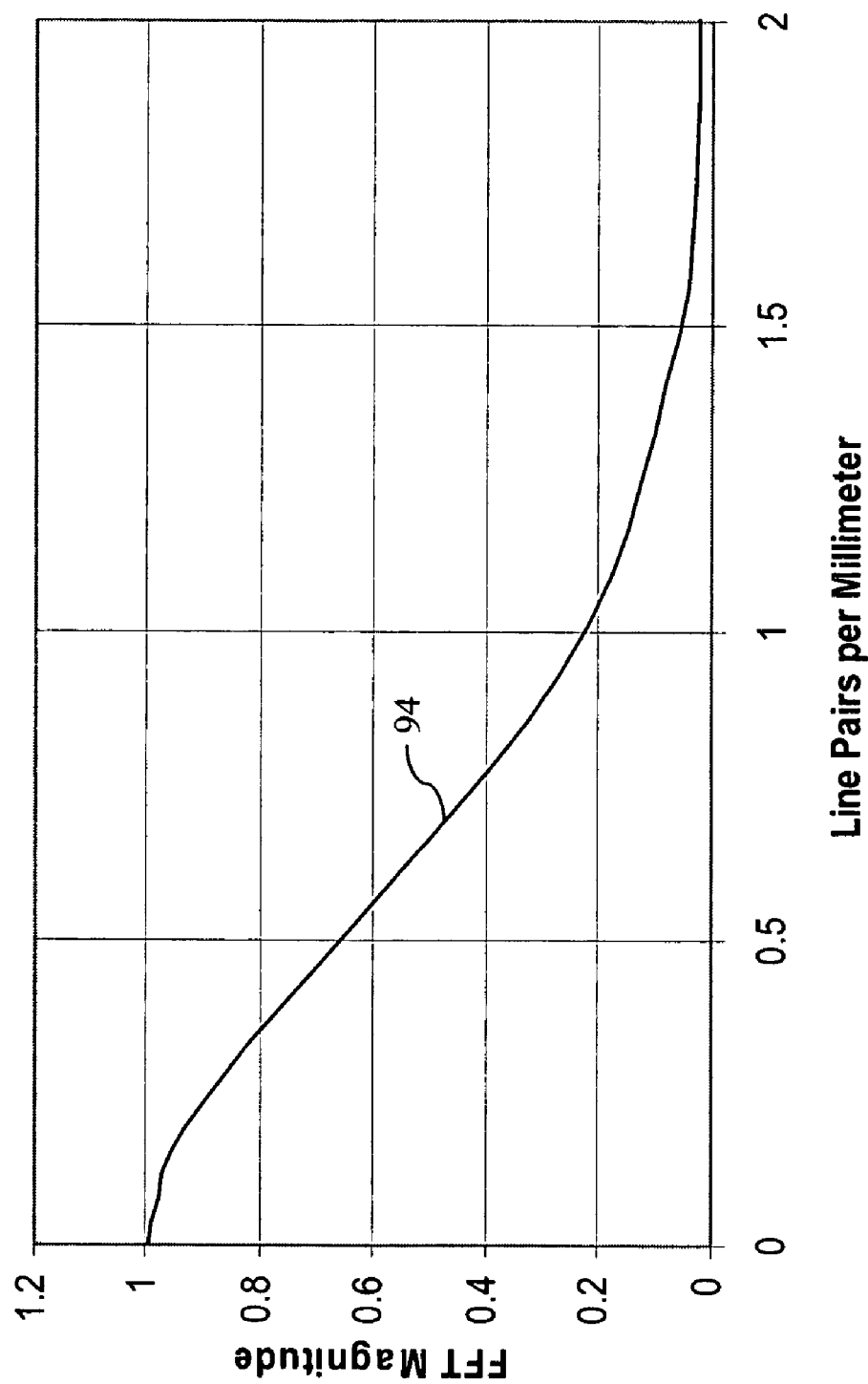
FIG. 6 is a graph showing the spatial frequency response at the focal plane of the digital imaging system.

Referring now to FIG. 6, there is shown the spatial frequency response 94 at the focal plane of the digital imaging system, which is one way to define the resolution of a digital imaging system. The spatial frequency response can be obtained by taking the Fast Fourier Transform (FFT) or other numerical analysis of the line spread function 93. Obtaining a numerical measure of the image resolution allows precise alignments and calibrations to be made to the digital imaging system so that the best possible images can be obtained therefrom.

As shown in FIG. 1, embodiments of this invention may also comprise several smaller phantoms 96 that are useful for measuring the focal uniformity over a larger section of the detector area. The same analysis that was described for the larger phantom 90 can also be used on each of these smaller phantoms 96. Such embodiments provide an accurate measurement of the focal uniformity of the detector across a fixed focal depth.

Figure 7:
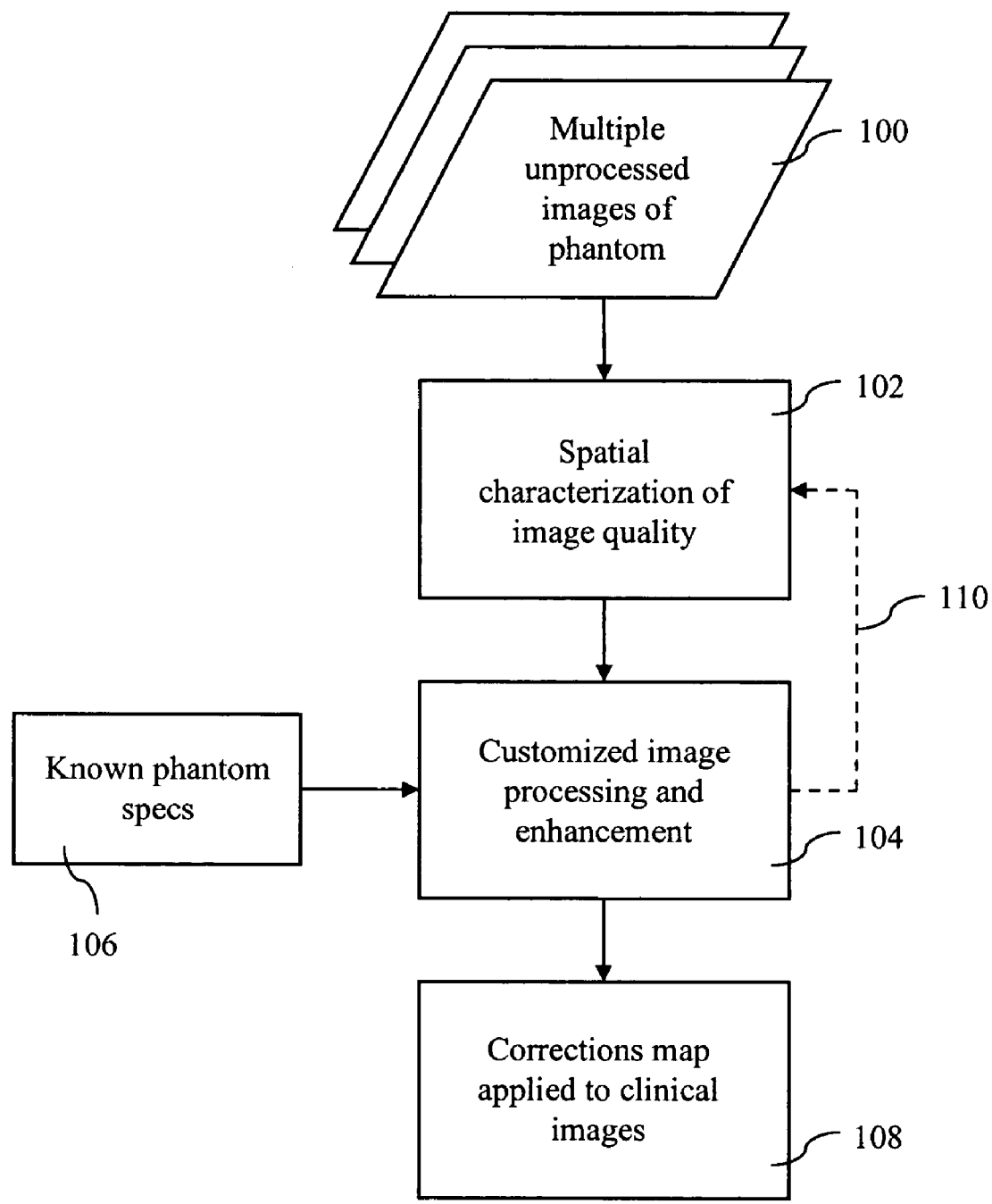
FIG. 7 is a flowchart showing the steps that are followed in embodiments of this invention to correct repeatable alignment errors in an effort to yield uniform image quality for maximum visualization of image structures.

In addition to characterizing image quality performance at different locations in the image, the output of the analysis of this invention can be used to correct, using image processing and filtering techniques, repeatable alignment errors in order to yield uniform image quality for maximum visualization of the objects that are imaged. As shown in FIG. 7, there is shown a flowchart showing the steps that are followed in embodiments of this invention to correct repeatable alignment errors. To isolate repeatable alignment errors from random alignment errors, multiple unprocessed images of the phantom(s) can be used 100. A spatial characterization of each image may then be made 102. Thereafter, customized image processing and enhancements may be made 104, and may take into account known phantom specifications 106 that have been previously determined. The image processing parameters may be adjusted as necessary 110 to optimize the image quality. Finally, a corrections map may be applied to the images 108, to produce final images that are free of repeatable alignment errors.

The phantoms and the alignment systems and methods described herein may be used in numerous radiographic imaging systems, for purposes such as, but not limited to, medical imaging (i.e., film-based x-ray systems, digital x-ray systems, linear tomography systems, tomosynthesis systems, computed radiography systems, and any other radiographic imaging systems and/or x-ray planographic imaging systems that allow the obtained images to be digitized so that numerical analysis can be made thereof, etc.), nondestructive imaging and/or testing of parts, and/or for detecting contraband (i.e., weapons, explosives, etc.).

As described above, by allowing for the precise alignment of radiographic imaging systems, this invention allows high quality images, having better image resolution than currently possible, to be achieved. Advantageously, the phantoms of this invention are simple to use and the results obtained therefrom are simple to analyze, making this solution particularly attractive. The phantoms of this invention allow the mechanical alignment of radiographic imaging systems to be accurately calibrated and validated. As a result thereof, improved image quality and optimal image resolution can be achieved with the present invention. Many other advantages will also be apparent to those skilled in the relevant art.

Various embodiments of this invention have been described in fulfillment of the various needs that the invention meets. It should be recognized that these embodiments are merely illustrative of the principles of various embodiments of the present invention. Numerous modifications and adaptations thereof will be apparent to those skilled in the art without departing from the spirit and scope of the present invention. For example, while the embodiments shown and described herein utilize a bar-shaped phantom, numerous other shapes are possible without deviating from the spirit and scope of this invention, and all such variations are intended to be covered herein. Thus, it is intended that the present invention cover all suitable modifications and variations as come within the scope of the appended claims and their equivalents.

What is claimed is:

1. A method for obtaining a quantitative measurement of the mechanical alignment, resolution, and resolution uniformity of a radiographic imaging system, the method comprising:
providing a radiographic imaging system comprising a two-dimensional rectangular imaging array;
providing a phantom having an edge used to obtain quantitative image resolution measurements, wherein the edge of the phantom is positioned on an extra-planar diagonal of said array of the radiographic imaging system;
obtaining a digital image of the phantom; and
analyzing the frequency content of a derivative of an edge of the image of the phantom to obtain a spatial frequency response of the radiographic imaging system,
wherein the spatial frequency response comprises the quantitative measurement of the mechanical alignment, resolution, and resolution uniformity of the radiographic imaging system.

2. The method of claim 1, wherein analyzing the frequency content of the derivative of the edge of the image of the phantom to obtain the spatial frequency response of the radiographic imaging system further comprises:
measuring the maximum possible resolution of the radiographic imaging system at a given focal plane to obtain a profile of the phantom.

3. The method of claim 2, further comprising the step of:
taking the derivative of the profile to obtain the line spread of the radiographic imaging system.

4. The method of claim 3, further comprising the step of:
analyzing the frequency content of the line spread to obtain the spatial frequency response of the radiographic imaging system.

5. The method of claim 1, further comprising utilizing a plurality of phantoms at different locations on said array so that the focal uniformity of an area of the array can be determined.

6. The method of claim 1, wherein the radiographic imaging system comprises at least one of: a digital imaging system, a digital x-ray system, a linear tomography system, a tomosynthesis system, a computed radiography system, a radiographic imaging system wherein the obtained images are digitized so that numerical analysis can be made thereof, and an x-ray planographic imaging system wherein the obtained images are digitized so that numerical analysis can be made thereof.

7. A method for mechanically aligning a radiographic imaging system, the method comprising the steps of:
(a) providing a radiographic imaging system comprising a two-dimensional rectangular imaging array;
(b) providing a phantom having an edge used to obtain quantitative image resolution measurements, wherein the edge of the phantom is positioned on an extra-planar diagonal of said array of the radiographic imaging system;
(c) obtaining a digital image of the phantom;
(d) obtaining a quantitative measurement of the mechanical alignment, resolution, and resolution uniformity of the radiographic imaging system; and
(e) aligning the radiographic imaging system once the quantitative measurement is obtained.

8. The method of claim 7, further comprising:
repeating steps (c)–(e) as necessary until the radiographic imaging system meets a predetermined alignment measurement.

* * * * *